US007968131B2

(12) United States Patent
Walter et al.

(10) Patent No.: US 7,968,131 B2
(45) Date of Patent: *Jun. 28, 2011

(54) CALCIUM-ENRICHED FOOD PRODUCT

(75) Inventors: Mary A. Walter, San Antonio, TX (US); Nick N. Davis, San Antonio, TX (US)

(73) Assignees: Mission Pharmacal Co., Boerne, TX (US); Sterling Foods, Ltd., San Antonio, TX (US)

( * ) Notice: Subject to any disclaimer, the term of this patent is extended or adjusted under 35 U.S.C. 154(b) by 609 days.

This patent is subject to a terminal disclaimer.

(21) Appl. No.: 11/468,077

(22) Filed: Aug. 29, 2006

(65) Prior Publication Data

US 2007/0160714 A1    Jul. 12, 2007

Related U.S. Application Data

(63) Continuation-in-part of application No. 11/329,905, filed on Jan. 11, 2006.

(51) Int. Cl.
*A23L 1/30* (2006.01)
(52) U.S. Cl. ........ 426/73; 426/72; 426/74; 426/94; 426/496; 426/549; 426/622
(58) Field of Classification Search ............. 426/72, 426/73, 549, 74, 94, 496, 622
See application file for complete search history.

(56) References Cited

U.S. PATENT DOCUMENTS

| 5,514,387 | A | 5/1996 | Zimmerman et al. |
| 6,086,927 | A | 7/2000 | Frielich et al. |
| 6,126,982 | A * | 10/2000 | Maldonado ............ 426/549 |
| 6,210,686 | B1 * | 4/2001 | Bell et al. ............... 424/400 |
| 6,495,191 | B1 | 12/2002 | Maldonado |
| 6,723,358 | B1 | 4/2004 | van Lengerich |
| 2001/0007690 | A1 * | 7/2001 | Girsh ...................... 426/442 |
| 2002/0022058 | A1 * | 2/2002 | Lovercheck ............. 424/601 |
| 2003/0108594 | A1 * | 6/2003 | Manning et al. ......... 424/439 |
| 2004/0047962 | A1 * | 3/2004 | Takaichi et al. ......... 426/549 |
| 2005/0100622 | A1 * | 5/2005 | Nair et al. ............... 424/777 |
| 2005/0170049 | A1 * | 8/2005 | Dibble et al. ............ 426/74 |

OTHER PUBLICATIONS

Heather Granato, Masking agents maximize functional foods' potential, Jan. 14, 2002, http://www.naturalproductsinsider.com/articles/211fbff1.html.*
Lillian May Ingsterand Manning Feinleib, Could Salicylates in Food Have Contributed to the Decline in Cardiovascular Disease Mortality? Sep. 1997, vol. 87, No. 9 http://www.ajph.org/cgi/reprint/87/9/1554.pdf.*

* cited by examiner

*Primary Examiner* — Brent T O'Hern
(74) *Attorney, Agent, or Firm* — Fulbright & Jaworski, LLP

(57) ABSTRACT

The present invention is directed to an enriched food product, such as a calcium-enriched chewable food product in which at least one piece of the food product provides the recommended daily DRI of elemental calcium. The enriched food product has a mouth feel, texture and taste substantially similar to a non-enriched food product. The food product may also provide Vitamin $D_3$ in a range of 100-2400 IU and optionally may be enrobed with a flavored coating. The present invention is also directed to a method for producing the enriched food product.

35 Claims, 3 Drawing Sheets

CALCIUM-ENRICHED FOOD PRODUCT

CROSS-REFERENCE TO RELATED APPLICATIONS

This application is a continuation-in-part of application Ser. No. 11/329,905 filed Jan. 11, 2006.

TECHNICAL FIELD

The present invention is directed to enriched food products and more particularly to a chewable calcium dietary supplement that can also function as a general delivery system for active ingredients.

BACKGROUND OF THE INVENTION

Calcium plays an important role in blood coagulation, nerve transmission, muscle contraction, and heart function. Protection against high blood pressure, colon cancer, and the degenerative bone disease known as osteoporosis have been attributed to calcium. Calcium is required in the diet in relatively large quantities. The Food and Nutrition Board has established a Dietary Reference Intake (DRI) for calcium. A daily intake of about 1000 mg of calcium meets most peoples needs for general health especially bone health. For older adults and people with osteoporosis many clinicians recommend a daily intake of about 1200 mg of calcium. Calcium requirements in adolescent children and lactating and pregnant women are 1000-1300 mg daily. The published DRIs list the recommended DRI by age. The daily adult upper limit "UL" of calcium is 2500 mg. See www.nal.usda.gov. However, the average calcium intake may be only about one-third to one-half of the recommended daily dosing. Thus, dietary supplementation of calcium is beneficial. If dietary sources of calcium do not provide sufficient amounts of calcium to the blood, calcium is depleted from the bones to compensate for the insufficient amounts. Age related bone loss and fracture rates in patients with osteoporosis may be reduced with high dietary intake of calcium. Calcium absorption efficiency decreases with increasing intake. Calcium absorption efficiency is greater if calcium is ingested in divided doses.

The ability of different individuals to utilize the calcium in food may vary considerably. For example, a high protein diet may result in about 15% of the dietary calcium being absorbed, whereas a low protein diet may result in only about 5% of the dietary calcium being absorbed. Moreover, changes in dietary protein in humans alter urinary calcium excretion. Increased protein consumption results in increased calcium excretion (Kerstetter, et al., Am J Clin Nutr 1998;68:859-865). Certain compounds in food may interfere with calcium absorption. Intestinal factors that influence the absorption of calcium include pH, the calcium:phosphorus ratio, the presence of free fatty acids which occurs when fat absorption is impaired, and the amount of vitamin D. Generally, the more alkaline the contents of the intestines, the less soluble are the calcium salts. Also, a high calcium:phosphorus ratio favors the formation of tricalcium phosphate rather than the more soluble, better absorbed forms. If either calcium or phosphorus is taken in excess, excretion of the other is increased. The optimal ratio is 1:1 when the intake of vitamin D is adequate. Vitamin D promotes the absorption of calcium from the intestine. Calcium citrate has been shown to have two independent mechanisms for calcium absorption, one is vitamin D dependent and one vitamin D independent (Favus and Pak; Am J of Therapeutics 2001;8:425-431). Many nutritionists believe that the current recommended daily levels of Vitamin $D_3$ (400 IU) are too low and advise higher levels.

Although milk has been a major source of calcium for infants and young children, many teenagers and adult Americans are consuming lesser amounts of it. The calcium content of milk and other beverages can be increased to facilitate meeting the U.S. DRIs for calcium. Calcium enrichment of other foods such as bean curd, yogurt, and cereal grains is disclosed in U.S. Pat. Nos. 4,676,583, 4,784,871, and 4,765,996, respectively.

Calcium compounds have been utilized in baked goods such as crackers, as components of leavening agents, as pH adjusters, in yeast foods, and for its nutritive value. However, calcium-fortified baked goods typically have a dry mouth feel, a dry and hard texture and a very chalky taste as compared to a noncalcium-fortified baked product.

U.S. Pat. No. 5,514,387 is directed to calcium-enriched baked goods and teaches the tenderization of calcium-enriched crackers and other baked goods in which the dough includes an emulsifying amount of at least one poly-oxyethylene sorbitan fatty acid ester and at least one stearoyl lactylate. U.S. Pat. No. 4,196,226 discloses a leavening acid comprising alkali metal aluminum phosphate granules having a calcium rich outer surface for improving flow and dusting properties. U.S. Pat. Nos. 6,495,191 and 6,126,982 disclose wheat flour for mineral-enhanced bakery products having at least an additional 2-20% by weight of dietary minerals.

It would be desirable to have a chewable calcium-enriched food product that meets the requirements for a Dietary Supplement that has acceptable mouth feel, appearance, taste, aroma, and texture in which at least one piece of the food product provides the recommended daily DRI of calcium and a Vitamin $D_3$ range of 100-2400 IU.

It would also be desirable to have a food product that can act as a delivery system for other active compounds such as other vitamins, multivitamins, beneficial oils and fats, actives (including dietary supplements and pharmaceuticals) and those ingredients that are needed in larger quantities than can be delivered in a tablet form.

BRIEF SUMMARY OF THE INVENTION

The present invention is directed to a calcium-enriched chewable food product in which at least one piece of the food product can provide the recommended daily DRI of calcium. The calcium-enriched food product has a mouth feel, texture and taste substantially similar to a non-calcium-enriched food product. The food product can be baked, unbaked, cooked, uncooked, or a confectionary. At least one piece of the food product provides calcium in the range of 100-1500 mg, preferably one piece of the food product provides calcium in the range of 100-650 mg and most preferably, the amount of calcium in each piece is 500 mg. At least one piece of the food product can further provide calcium in the range of 100-490 mg calcium. Each piece of the food product also provides Vitamin $D_3$ in a range of 100-2400 IU.

Optionally, the food product can be enrobed with a flavored coating.

The calcium is selected from a group of elemental calcium sources consisting of calcium citrate, calcium gluconate, calcium lactate, calcium carbonate, calcium phosphate and calcium citrate malate. In the food product, less than 100% of the calcium citrate has a particle size less than 100 μm; less than 99% of the calcium citrate has a particle size less than 40 μm; and less than 90% of the calcium citrate has a particle size less than 20 μm. The preferred median particle size is 2-6 μm.

The food product is selected from a group consisting of a confectionary, a flavored cake, a brownie, a strudel and other cake-like products. The food product can have either a bakery type interior or a confectionary type interior and optionally is enrobed with a flavored coating.

The food product has a flavor selected from a group consisting of chocolate, chocolate mint, lemon, caramel, cappuccino, mocha, cinnamon, maple, butter, fruit flavors, vanilla, peanut butter, and carrot cake flavor.

The coating has a flavor selected from a group consisting of chocolate, chocolate mint, lemon, caramel cappuccino, mocha, cinnamon, maple, butter, fruit flavors, vanilla, yogurt and peanut butter.

Each piece of the unenrobed food product has a weight preferably in the range of 3.5 to 24 grams and each piece of the food product can optionally be completely enrobed with 0.5-8 grams of coating.

The present invention is also directed to a method for producing an enriched food product, the food product being chewable and providing the recommended daily DRI of calcium. The method includes the steps of: a) mixing selected wet and dry ingredients in a mixer to form a mixed dough/batter; b) feeding the mixed dough/batter through an extruder; c) cutting the extruded dough/batter into individual pieces d) enrobing the individual pieces; and e) packing the pieces into any number of packaging configurations such as trays. The method thereby provides a chewable calcium-enriched food product in which at least one piece of the food product provides the recommended daily DRI of calcium and the food product has a mouth feel, texture and taste substantially similar to a non-calcium-enriched food product.

The present invention is further directed to a chewable enriched food product in which at least one piece of the food product is a delivery system for active compounds, beneficial oils and fats, dietary supplements, pharmaceuticals and/or additives; wherein the enriched food product has a mouth feel, texture and taste substantially similar to a non-enriched food product.

The active compounds are selected from a group consisting of minerals such as magnesium, manganese, zinc, magnesium, iron, and phosphorus; vitamins such as Vitamin A, the Vitamin B group, Vitamin C, D and K.

The beneficial oils and fats are selected from a group consisting of DHA (docosahexaenoic acid), omega 6 and 3 fatty acids The active compounds are further selected from a group consisting of functional ingredients such as antioxidant and other related compounds, glucosamine, and chondroitin.

The pharmaceuticals are selected from a group consisting of phenyltoin, cholchicine, ibuprofen, aspirin, hydroxchloroquine, and diuretics.

The additives are selected from a group consisting of caffeine, flavor masking agents, microencapsulated active compounds, and light, heat and temperature liable compounds.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
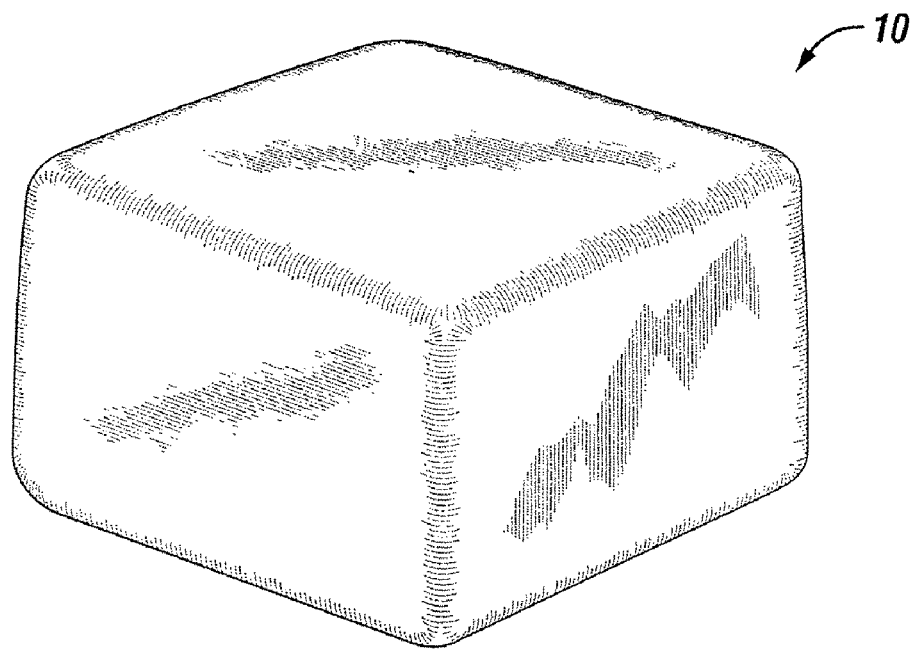
FIG. 1 is a perspective view of the inventive food product.

As used herein, the use of the word "a" or "an" when used in conjunction with the term "comprising" in the claims and/or the specification may mean "one," but it is also consistent with the meaning of "one or more," "at least one," and "one or more than one."

A confectionary is defined as candy and other sweet items of snack food. Within the context of this specification, the term does not include cakes, biscuits, brownies or other cake-like products.

Water activity is a measurement of the energy status of the water in a system; represented by a quotient between water's partial pressure in the food and pure water's partial pressure. It indicates how tightly water is bound, structurally or chemically, within a substance. This is measured by equilibrating the liquid phase (in the sample) with the vapor phase (in the headspace) and measuring the relative humidity of that space. A major application of water activity concerns the control of microbial growth. The control of microbial growth is a significant component of food safety. Most pathogenic bacterial growth in food products can be stopped by water activity (aw)$\leq$0.85. To stop yeast and mold growth it is necessary to have aw$\leq$0.75. Moisture is a quantitative analysis to determine the total amount of water present in a sample.

Sources of calcium that are micronized have particles of a very small size, for example less than 100% of the micronized calcium particles are less than 100 μm in size.

Mouthfeel is the mingled experience deriving from the sensations of the mucus membrane in the mouth during and/or after ingestion of a food or beverage. It relates to density, moisture, viscosity, surface tension and other physical properties of the food or beverage being sampled.

A daily intake of about 1000 mg of calcium is the recommended Dietary Reference Intake (DRI) for calcium that meets most peoples needs (19-50 yrs) for general health, especially bone health. For older adults (over 50 yrs) and people with osteoporosis the recommend DRI is about 1200 up to 1500 mg of calcium, depending upon bone health. The required DRI of calcium in adolescent children (9-18 yrs) and lactating and pregnant women is about 1300 mg daily. The required DRI of calcium for infants 7-12 months is 270 gm daily, for young children 1-3 yrs is 500 gm daily, and children 4-8 is 800 mg daily.

As known to one skilled in the art of food technology, creamy is generally specified as having a combination of moderate to high viscosity, non-Newtonian flow, the presence of some fat and other factors. Foods that are creamy are very smooth and have to be free from gritty, lumpy, grainy or abrasive properties.

Other sources of calcium such as calcium gluconate, calcium lactate, calcium carbonate, and calcium citrate malate can be used as well as other known calcium sources. Preferably, the calcium sources have a lead level that is less than 0.10 μ per one gram of calcium source and more preferably less than 0.020 μ per one gram of calcium source.

Each unenrobed chewable piece can be formed into various sizes and weights. Examples of different sizes and weights are shown in the table below with the respective amount of calcium, Vitamin $D_3$, and calories for each.

| Weight | Elemental Calcium | % Elemental Calcium | Vitamin $D_3$ | Calories | Size |
|---|---|---|---|---|---|
| 3.5 grams +/− 5% | 100-500 mg, preferably 250 mg | 2.86-14.29% preferably 7.14% | 100-600 IU | 14-16 | 3/8" length, " 7/8 width, " 2/3 height |
| 9 grams +/− 3% | 100-650 mg, preferably 500 mg | 1.11-7.22% preferably 5.56% | 200-1200 IU | 35-40 | 7/8" length, " 7/8 width, " 2/3 height |
| 18 grams +/− 3% | 500-1200 mg, preferably 1000 mg | 2.78%-6.67% preferably 5.56% | 400-2400 IU | 70-80 | 1 3/4" length, 7/8" width, " 2/3 height |
| 24 grams +/− 3% | 500-1500 mg, preferably 1300 mg | 2.08-6.25% preferably 5.42% | 400-2400 IU | 90-110 | 2 1/3" length, 7/8" width, " 2/3 height |

Non-calcium enriched food products have a soft texture, an acceptable moist mouthfeel, do not have an off-taste, and are free of gritty and grainy properties. Increasing the calcium content of food products typically adversely affects the mouthfeel, taste and texture of the food product, resulting in a food product that has a dry mouthfeel, a caulky taste and a hard texture.

In the present invention, it has been found that the calcium content of the chewable food product can be increased by the use of a micronized calcium source. The use of micronized calcium, preferably calcium citrate, results in a food product that has an acceptable moist mouthfeel, a soft texture and a taste that is comparable to a non-calcium -enriched food product.

Figure 2:
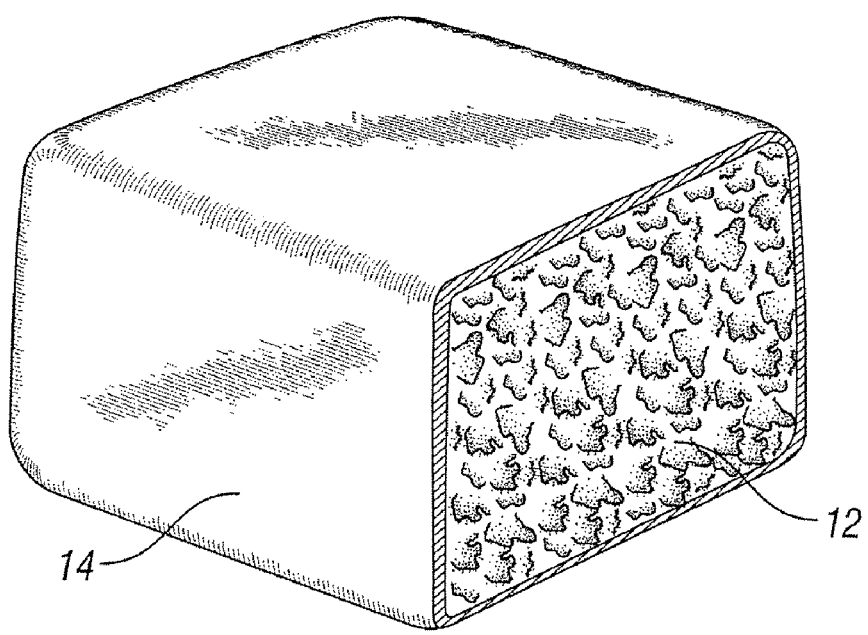
FIG. 2 is a perspective view of the food product of FIG. 1 showing the interior of the food product.

The food product 10 of the present invention can include for example a confectionary, a flavored cake, a brownie, or a strudel or other cake-like product (FIG. 1). The food product can be baked, unbaked, cooked or uncooked. The food product preferably has a bakery or confectionary-type interior and an optional exterior coating. Preferably, the mouthfeel is creamy and smooth. In a preferred embodiment, the chewable food product 10 is a flavored cake or confectionary 12, optionally enrobed in a flavored coating 14 (FIG. 2). The product can contain calcium citrate and also Vitamin $D_3$. Any flavoring can be used for the cake/confectionary and coating. Some examples of flavorings can be selected from flavors such as chocolate, chocolate mint, lemon, caramel, cappuccino, mocha, cinnamon, maple, butter, fruit flavors, vanilla, peanut butter, and a carrot cake flavoring, each with an appropriate coating.

Preferably, the calcium source is "calcium citrate tetrahydrate, USP Ultra Fine" from suppliers such as Jost Chemical Co, Inc. St. Louis, Mo.; Jungbunzlauer Ladenburg GmbH, Ladenburg; or Boehringer Ingelheim GmbH, Ingelheim Germany. In a preferred embodiment, less than 100% of the calcium source has a particle size less than 100 μm. In a more preferred embodiment, less than 99% of the calcium source has a particle size below 40 μm. In a most preferred embodiment, less than 90% of the calcium source has a particle size below 20 μm, with a median particle size between 2-6 μm.

The chewable food product has a moisture content of 13-15%, preferably 14%, and a water activity of less than 0.8, preferably less than 0.75 and more preferably between 0.60 and 0.65. The shelf-stability of the food product is between 1 to 36 months. The enrobed food product can have the following amount of coating: 3.5 gm piece can have about 0.5-2 gm of coating, preferably 1 gm; 9 gm piece can have about 1.5-4 gm of coating, preferably 2 gm; 18 gm piece can have about 3-6 gm of coating, preferably 4 gm; and the 24 gm piece can have about 4-8 gm of coating, preferably 5.5 gm.

At least one piece of the chewable food product can provide the recommended daily DRI of calcium depending upon the age of the person and the size of the food product. The chewable food product also has no trans fat, a low lead level and is low in carbohydrates. The amount of calcium in each piece will depend upon the size of the chewable piece or the size can be kept constant and the amount of calcium varied. For example, a piece weighing 3.5-9 grams can provide calcium in the range of 100-650 mg (1.11% - 18.57% calcium by weight). Two 9 gram pieces having 500 mg calcium each (5.56% calcium by weight each), can provide a daily DRI of 1000 mg of calcium. Therefore, the number of pieces that will meet the recommended daily DRI for calcium will depend upon the size and weight of the chewable piece. However, calcium absorption efficiency is greater if calcium is ingested in divided doses.

The ingredients in the food product can include for example, sugar, calcium citrate, enriched bleached flour (niacin, reduced iron, thiamine mononitrate, riboflavin, folic acid), milk, egg, oils such as partially hydrogenated palm kernel and palm oils and soybean oil, corn syrup, whey, natural and artificial flavors, cocoa, xanthan gum, glycerol, soy lecithin, artificial colors, sodium benzoate, phosphoric acid, potassium sorbate, salt, and Vitamin $D_3$. In an alternate embodiment, DHA can be an additional ingredient or can replace any of the oils, such as soybean oil. Preferably, the milk and eggs are dried and should be pasteurized for safety reasons because the food product is not baked or cooked other than "the cooking" that takes place as the ingredients pass thorough the extruder. In alternate embodiments, the dried eggs or the nonfat dry milk or both can be replaced with dextrose, fructose, malto-dextrin, flour, sucrose (powdered sugar) or starch. Invertase can be added to maintain a soft texture. Invertase, is an enzyme that helps maintain a product's soft texture by breaking down the sucrose. Fat emulsifiers such as lecithin, mono- and diglycerides, propylene glycol, and mono esters of fatty acids may be used to emulsify the oils in order to retard oil migration within the morsel. Further, ingredients with undesirable taste profiles can be enrobed to mask the unpleasant taste. The food product can optionally be enrobed with a flavored coating.

The chewable food product 10 of the present invention has an extended shelf-life, preferably a shelf-life of 1-36 months, more preferably 18-24 months. This is achieved by reducing both the oxygen level and the water activity of the product. Preferably, the oxygen level is as low as possible without producing changes to the flavor or appearance of the product. The deterioration of foods by microorganisms can take place rapidly during storage. Moisture content is an important factor in controlling the rate of deterioration in food products. It is the availability of water for microbial activity that determines the shelf-life of a food and this is measured by the water activity of a food. Thus, it is desirable that the water activity of the chewable food product be less than 0.8 and preferably less than 0.75. Therefore, a low oxygen level and a water activity level less than 0.8 provides for a fresh tasting and stable product that will remain for the product's shelf-life of 1-36 months.

The chewable food product 10 can also function as a delivery system for other minerals such as magnesium, manganese, zinc, magnesium, iron, and phosphorus, other vitamins such as Vitamin A, the Vitamin B group, Vitamin C, D and K, DHA (docosahexaenoic acid), omega 6 and 3 fatty acids, functional ingredients such as antioxidant and other related compounds, glucosamine, chondroitin, caffeine, drug-active pharmaceutical ingredients, such as phenyltoin, cholchicine, ibuprofen, aspirin, hydroxchloroquine, diuretics, flavor masking agents, microencapsulated active compounds and any number of light, heat and temperature liable compounds. As a delivery system, food product 10 can also provide a means of delivering doses of drug-active pharmaceutical ingredients that are too large to be delivered in tablet form. This is not an exhaustive list of contemplated ingredients and compounds.

Figure 3:
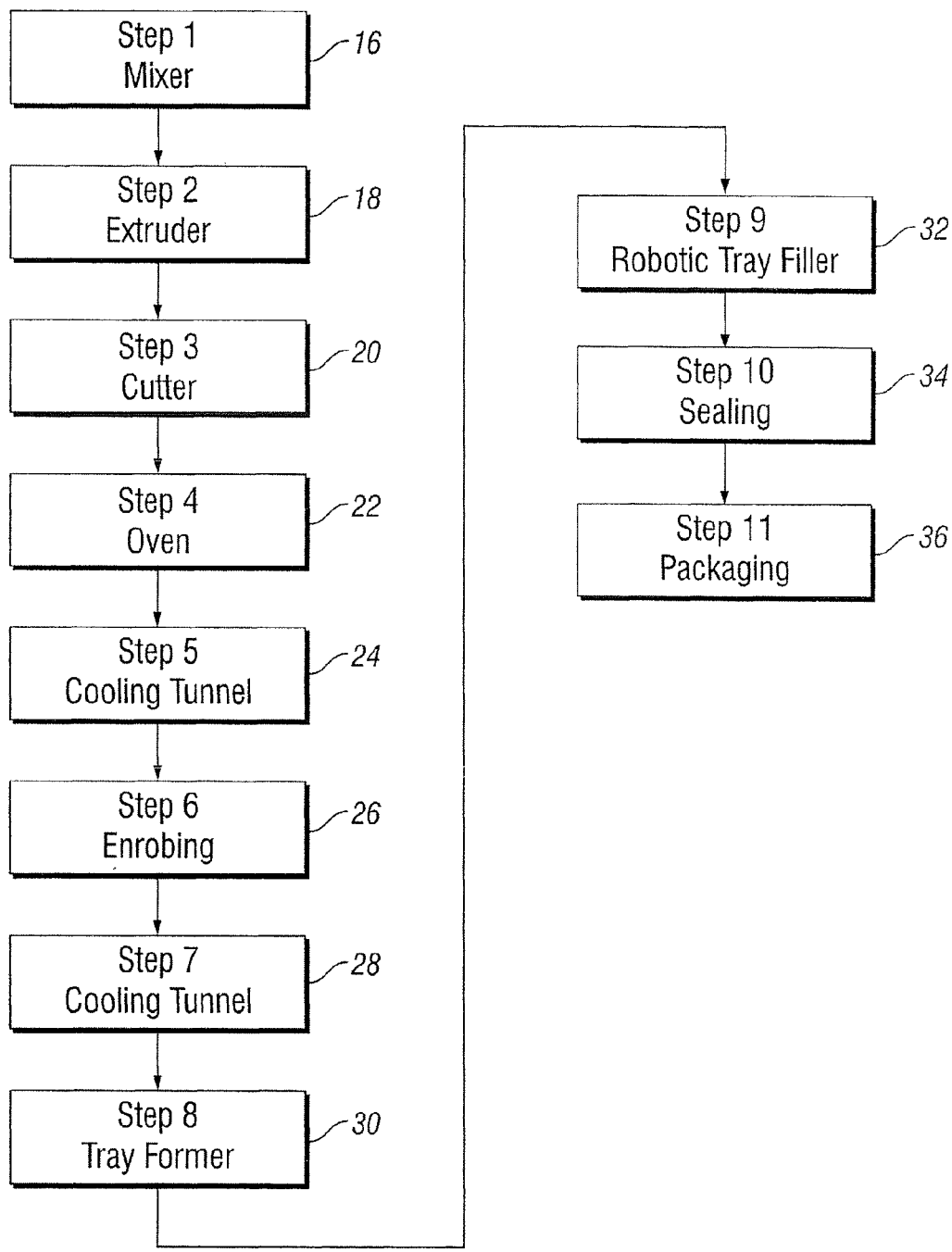
FIG. 3 is a flow chart of the process steps for producing the inventive food product.

As illustrated in the flow chart of FIG. 3, the chewable food product of the present invention is formed by mixing the dry ingredients and wet ingredients in a mixer 16. In a preferred embodiment, a vertical mixer is used. Mixing is timed to ensure content uniformity of all ingredients, especially the active ingredients. The mixed dough/batter is fed through an extruder 18, such as a twin screw extruder. In a preferred embodiment, a ve-mag extruder is used because of the need to minimize the entrapped air in the food product. This is because entrapped air will cause weight variation of the food product and in order for food products to be suitable as a dietary supplement, certain weight tolerances need to be met. In a most preferred embodiment, the ve-mag extruder has a vacuum chamber to keep the extruder head filled at a constant level and to provide positive pressure to the twin extruder. It has surprisingly been found that the extruded dough/batter does not require baking or additional cooking, beyond any "cooking" that takes place in the extrusion process, to achieve a bakery or confectionary-like texture.

The extruded dough/batter is cut 20 into pieces, preferably with a double reciprocating guillotine. One can optimize the dough consistency for ease of extrusion. Changing the timing of the guillotine cutting and the conveyor speed will result in a food product of varying concentration of the calcium, Vitamin $D_3$ and other delivery system ingredients. Alternatively, the amount of calcium, Vitamin $D_3$ and delivery system ingredients in the dough mixture can be varied and the food product size kept constant. This allows for a customization of the food product to meet the varying recommended daily DRIs for calcium or other recommended doses.

After extruding, the product is cooled in a cooling tunnel 24 to the ambient temperature of the process room. The immediate cooling minimizes degradation of the Vitamin $D_3$ and other heat and light liable ingredients. Thereafter, each piece can be enrobed 26 with a coating using a standard confectionary enrober known to one skilled in the art of food production. In a preferred embodiment, each piece is completely enrobed with a coating. For example the 3.5 gm piece can have about 0.5-2 gm of coating, preferably 1 gm; the 9 gm piece can have about 1.5-4 gm of coating, preferably 2 gm; the 18 gm piece can have about 3-6 gm of coating, preferably 4 gm; and the 24 gm piece can have about 4-8 gm of coating, preferably 5.5 gm. The coating totally encapsulates each piece substantially protecting the Vitamin $D_3$ and other labile vitamins and ingredients from light and certain oxygen sources that can cause degradation. Once the product is enrobed it travels again through a cooling tunnel 28 in order to set the coating.

One skilled in the art of food technology knows that the contemplated shipping conditions of an enrobed food product will impact the choice of the enrobing material. Generally, if a low melt point enrobing material in the range of 102-110° F. is used, the enrobed food product will require refrigerated or controlled cool shipping conditions. Alternatively, if a high melt point enrobing material in the range of 110-130° F. is used, the enrobed food material can be shipped under non-refrigerated conditions and will withstand adverse environmental conditions in most places. In a preferred embodiment, a high melt point enrobing material, having a melt point of 117° F., can be used in order to prevent the coating from melting during most shipping conditions. The enrobing material can be obtained from sources such as Guittard Chocolate Company, Burlingame, Calif.; AMD, Decatur, Ill. or Clasen Quality Coating, Inc., Madison, Wis.

After the coating has set, the product may be transferred to a packing area via conveyors or by moving manually. A standard horizontal form, fill and seal machine is used. In a preferred embodiment, a high barrier laminated film structure is thermo-formed into "blister" cavity trays 30 and a robotic pick and place system 32 fills the trays with the chewable food product. The filled trays pass into a sealing station 34 where the atmosphere is modified to remove oxygen from the headspace of the tray cavity and replace it with inert gas. In a preferred embodiment, the inert gas is composed of 0-20% carbon dioxide and 80-100% nitrogen. The trays are hermetically sealed with a foil laminate film having certain barrier properties. In a preferred embodiment, the foil laminate film has an Oxygen Transmission Rate of 0.019-0.026 cc/(100 in$^2$ day) and a Water Vapor Transmission Rate of 0.068, ±3% gm/(100 in$^2$ day). The product is thereafter loaded into a variety of retail packaging configurations 36.

Figure 4:
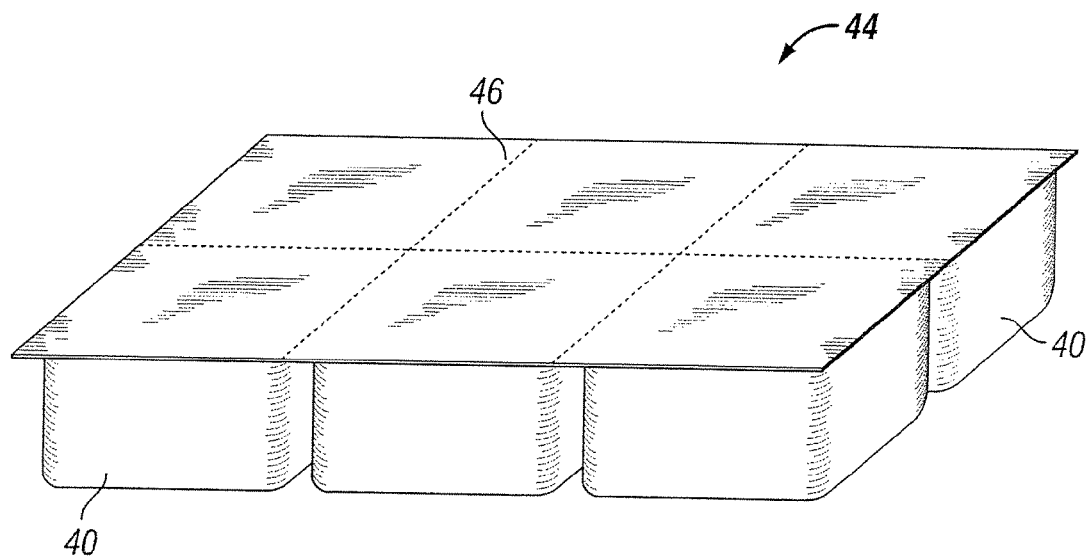
FIG. 4 is a perspective view of packaging for a single serving of the food product of FIG. 1.
Figure 5:
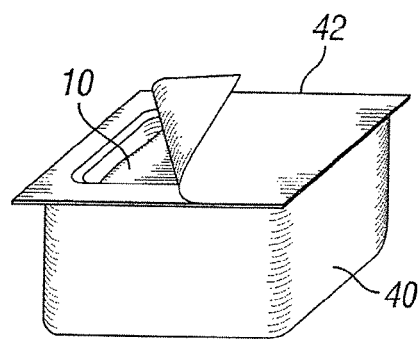
FIG. 5 is a perspective view of an embodiment of a multi-pack formed from the packaging of FIG. 4.

In one example of the packaging 38, the each piece of the food product 10 is placed in an individual tray 40 having a foil laminate film 42 (FIG. 4). The trays 40 can be configured in a pack 44 consisting of two rows of three trays each in which the edges of the trays 40 have perforations 46 for easy separation (FIG. 5).

It is understood that all processing steps can be performed manually without the need for mixers, extruders, cutters, cooling tunnels or automated packaging devices.

The present invention is further illustrated in the following examples, where all parts, ratios and percentages are by weight, and all temperatures are in ° F., unless otherwise stated:

EXAMPLE 1

One example is a 9 gram sized brownie or chocolate confectionary product that is dipped in a chocolate flavored coating. The ingredients and their relative amounts may be used to produce a calcium enriched brownie/confectionary that provides about 500 mg calcium and about 200 IU of Vitamin $D_3$,

| Brownie/Confectionary Ingredients | w/w % |
| --- | --- |
| Powder sugar | 27-30% |
| Cake flour | 11-14% |
| Whole eggs dried | 1-4% |
| Corn starch | 0.3-1.3% |
| Nonfat dry milk | 0.9-2.5% |
| Cocoa powder | 0.5-2.5% |
| Xanthan gum | 0.25-0.4% |
| Salt | 0.5-1.5% |
| Calcium Citrate | 26.6-28.6% |
| Potassium Sorbate | 0.075-0.15% |
| Water | 6-9% |
| Corn syrup | 2.5-4% |
| Glycerol | 0.5-1.5% |
| Soy or palm oil | 6-9% |
| Vanilla extract | 0.15-0.7% |
| Chocolate extract | 1.5-3.5% |
| Brown color | 0.009-.015% |
| Coffee emulsion | 0.002-0.01% |
| Vitamin $D_3$ (100,000 IU/G) | 0.029-.035% |

The dry and wet ingredients for the brownie/chocolate confectionary are mixed in a vertical mixer and the mixed batter is fed through a ve-mag extruder. In an alternate embodiment, dextrose can be substituted on an equal w/w % basis for either the dried eggs, the dry milk or both. Invertase can also be added. The extruded product is cut into pieces with a double reciprocating guillotine. Thereafter, the product is cooled to the ambient temperature of the process room.

Each piece is enrobed with about 2 grams of a chocolate flavored coating using a standard chocolate enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 2

Another example is a 9 gram piece of lemon flavored cake or confectionary dipped in a lemon flavored coating. The ingredients and their relative amounts may be used to produce a calcium enriched cake/confectionary that provides about 500 mg calcium and about 200 IU of Vitamin $D_3$.

| Cake/Confectionary Ingredients | w/w % |
| --- | --- |
| Powder sugar | 29-32% |
| Cake flour | 13-16% |
| Whole eggs dried | 1.5-3.0% |
| Corn starch | 0.2-1% |
| Nonfat dry milk | 0.5-2.5% |
| Xanthan gum | 0.2-0.65% |
| Salt | 0.5-1.5% |
| Calcium Citrate | 26.6-28.6% |
| Potassium Sorbate | 0.06-1.1% |
| Corn syrup | 2-4% |
| Glycerol | 0.8-2% |
| Soy or palm oil | 6-9% |
| Water | 6-9% |
| Vanilla extract | 0.2-1.1% |
| Yellow color | 0.003-.009% |
| Lemon extract, concentrated | 0.3-1.2% |
| Vitamin $D_3$ (100,000 IU/G) | 0.029-.035% |

The dry and wet ingredients for the cake are mixed in a vertical mixer and the mixed batter is fed through a ve-mag extruder. In an alternate embodiment, dextrose can be substituted on an equal w/w % basis for either the dried eggs, the dry milk or both. Invertase can also be added. The extruded product is cut into pieces with a double reciprocating guillotine. Thereafter, the product is cooled to the ambient temperature of the process room.

Each piece is enrobed with about 2 grams of a lemon flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 3

Another example is a 9 gram piece of caramel flavored cake or confectionary dipped in a caramel flavored coating. The ingredients and their relative amounts may be used to produce a calcium enriched cake/confectionary that provides about 500 mg calcium and about 200 IU of Vitamin $D_3$.

| Cake/Confectionary Ingredients | w/w % |
| --- | --- |
| Powder sugar | 28-32% |
| Cake flour | 13-16% |
| Whole eggs dried | 1.5-3% |
| Corn starch | 0.3-1.1% |
| Nonfat dry milk | 0.8-2.2% |
| Xanthan gum | 0.1-0.5% |
| Salt | 0.5-1.5% |
| Calcium Citrate | 26.6-28.6% |
| Potassium Sorbate | 0.08-0.13% |
| Corn syrup | 1.9-3.5% |
| Glycerol | 0.75-1.5% |
| Soy or palm oil | 6-9% |
| Water | 7-9% |
| Vanilla extract | 0.1-1.3% |
| Yellow color | 0.008-.012% |
| Caramel flavor | 1-3% |
| Caramel color | 0.01-0.09% |
| Vitamin $D_3$ (100,000 IU/G) | 0.029-.035% |

The dry and wet ingredients for the cake are mixed in a vertical mixer and the mixed batter is fed through a ve-mag extruder. In an alternate embodiment, dextrose can be substituted on an equal w/w % basis for either the dried eggs, the dry milk or both. Invertase can also be added. The extruded product is cut into pieces with a double reciprocating guillotine. Thereafter, the product is cooled to the ambient temperature of the process room.

Each piece is enrobed with about 2 grams of a caramel flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 4

Another example is a 9 gram piece of chocolate mint flavored cake or confectionary dipped in a chocolate mint flavored coating. The ingredients and their relative amounts may be used to produce a calcium enriched cake/confectionary that provides about 500 mg calcium and about 200 IU of Vitamin $D_3$

| Cake/Confectionary Ingredients | w/w % |
|---|---|
| Powder sugar | 26-29% |
| Cake flour | 11-14% |
| Whole eggs dried | 1.5-3% |
| Corn starch | 0.3-1.1% |
| Nonfat dry milk | 0.9-2.5% |
| Cocoa powder | 0.9-2.5% |
| Xanthan gum | 0.1-0.6% |
| Salt | 0.6-1.3% |
| Calcium Citrate | 26.6-28.6% |
| Potassium Sorbate | 0.09-0.13% |
| Water | 5-8% |
| Corn syrup | 2.5-3.9% |
| Glycerol | 0.75-2% |
| Soy or palm oil | 6-9% |
| Vanilla extract | 0.1-1.5% |
| Mint flavor | 2-4% |
| Vitamin $D_3$ (100,000 IU/G) | 0.029-.035% |

The dry and wet ingredients for the cake are mixed in a vertical mixer and the mixed batter is fed through a ve-mag extruder. In an alternate embodiment, dextrose can be substituted on an equal w/w % basis for either the dried eggs, the dry milk or both. Invertase can also be added. The extruded product is cut into pieces with a double reciprocating guillotine. Thereafter, the product is cooled to the ambient temperature of the process room.

Each piece is enrobed with about 2 grams of a chocolate mint flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 5

Another example is a 9 gram piece of a calcium and multi-vitamin enriched lemon flavored cake or confectionary dipped in a lemon flavored coating. The ingredients and their relative amounts may be used to produce a multi-vitamin enriched cake/confectionary that provides 100-490 mg calcium, about 200 IU of Vitamin $D_3$, and a multi-vitamin mixture containing Vitamins D, A, E, B12, C, Beta carotene, folic acid, pantothenic acid, biotin, niacin, pyridoxine, thiamin, and riboflavin. The B vitamins preferably are enrobed for masking their taste.

| Cake/Confectionary Ingredients | w/w % |
|---|---|
| Powder sugar | 31-41% |
| Cake flour | 2-8% |
| Emulsifier | 1-3% |
| Corn starch | 0.5-1.5% |
| Nonfat dry milk | 1-2% |
| Xanthan gum | 0.25-0.50% |
| Salt | 0.5-1.5% |
| Calcium Citrate | 8-12% |
| Potassium Sorbate | 0.07-1.13% |
| Corn syrup | 2-4% |
| Glycerin | 1-3% |
| Palm oil | 5-8% |
| Water | 6-10% |
| Vanilla extract | 0.5-0.8% |
| Yellow color | 0.005-0.015% |
| Lemon extract, concentrated | 1-3% |
| Vitamin $D_3$ (100,000 IU/G) | 0.065-0.085% |
| Vitamin Blend | 1-3% |
| Vitamin C | 0.5-1% |
| MaltoDextrin | 15-20% |

The dry and wet ingredients for the cake are mixed in a vertical mixer and the mixed batter is fed through a ve-mag extruder. In an alternate embodiment, dextrose can be substituted on an equal w/w % basis for the dry milk. Invertase can also be added. The extruded product is cut into pieces with a double reciprocating guillotine. Thereafter, the product is cooled to the ambient temperature of the process room.

Each piece is enrobed with about 2 grams of a lemon flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 6

Another example is a 9 gram piece of a calcium and DHA enriched lemon flavored cake or confectionary dipped in a lemon flavored coating. The ingredients and their relative amounts may be used to produce an enriched cake/confectionary that provides about 500 mg calcium, about 200 IU of Vitamin $D_3$ and DHA.

| Cake/Confectionary Ingredients | w/w % |
|---|---|
| Powder sugar | 31-41% |
| Cake flour | 2-8% |
| Emulsifier | 0.25-0.75% |
| Corn starch | 0.5-1.5% |
| Nonfat dry milk | 1-2% |
| Xanthan gum | 0.25-0.50% |
| Salt | 0.5-1.5% |
| Calcium Citrate | 22-30% |
| Potassium Sorbate | 0.07-1.13% |
| Corn syrup | 2-4% |
| Glycerin | 1-3% |
| DHA oil | 5-10% |
| Water | 6-10% |
| Vanilla extract | 0.5-0.8% |

-continued

| Cake/Confectionary Ingredients | w/w % |
|---|---|
| Yellow color | 0.005-0.015% |
| Lemon extract, concentrated | 1-3% |
| Vitamin D | 0.035-0.065% |
| MaltoDextrin | 5-8% |

The dry and wet ingredients for the cake are mixed in a vertical mixer and the mixed batter is fed through a ve-mag extruder. In an alternate embodiment, dextrose can be substituted on an equal w/w % basis for the dry milk. Invertase can also be added. The extruded product is cut into pieces with a double reciprocating guillotine. Thereafter, the product is cooled to the ambient temperature of the process room.

Each piece is enrobed with about 2 grams of a lemon flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

EXAMPLE 7

Another example is a 9 gram piece of a multi-vitamin enriched lemon flavored cake or confectionary dipped in a lemon flavored coating. The ingredients and their relative amounts may be used to produce a multi-vitamin enriched cake/confectionary that provides a multi-vitamin mixture containing Vitamins D, A, E, B12, C, Beta carotene, folic acid, pantothenic acid, biotin, niacin, pyridoxine, thiamin, and riboflavin. The B vitamins preferably are enrobed for masking their taste.

| Cake/Confectionary Ingredients | w/w % |
|---|---|
| Powder sugar | 32-45% |
| Cake flour | 12-18% |
| Emulsifier | 0.5-1.0% |
| Corn starch | 0.5-1.5% |
| Nonfat dry milk | 2-3% |
| Xanthan gum | 0.5-0.75% |
| Salt | 0.5-1.5% |
| Potassium Sorbate | 0.07-1.15% |
| Corn syrup | 5-7% |
| Glycerin | 1-3% |
| Soy or palm oil | 8-12% |
| Water | 7-9% |
| Vanilla extract | 0.5-0.8% |
| Yellow color | 0.005-0.015% |
| Lemon extract, concentrated | 1-3% |
| Vitamin Blend | 1-3% |
| MaltoDextrin | 7-9% |

The dry and wet ingredients for the cake are mixed in a vertical mixer and the mixed batter is fed through a ve-mag extruder. In an alternate embodiment, dextrose can be substituted on an equal w/w % basis for the dry milk. Invertase can also be added. The extruded product is cut into pieces with a double reciprocating guillotine. Thereafter, the product is cooled to the ambient temperature of the process room.

Each piece is enrobed with about 2 grams of a lemon flavored coating using a standard enrober set up. Once the pieces are enrobed they travel through a cooling tunnel in order to set the coating. After the coating has set, the pieces are transferred to a packing area for packaging into "blister" cavity trays. The filled trays are hermetically sealed with a foil laminate film. The filled trays are thereafter loaded into a variety of retail packaging configurations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A calcium-enriched food product comprising:
a calcium-enriched chewable food product with a mouth feel, texture and taste substantially similar to a non-calcium-enriched food product;
wherein the calcium-enriched food product comprises between 2.78% and 18.57% elemental calcium and the source of the elemental calcium is calcium citrate with a median particle size between about 3 µm to 6 µm;
wherein the calcium-enriched food product has a moisture content of 13-15% by weight;
wherein the calcium-enriched food product provides Vitamin $D_3$ in a range of 100-2400 IU; and,
wherein the calcium-enriched food product has a water activity of less than 0.8.

2. The food product of claim 1, wherein the food product provides calcium in the range of 100-1500 mg.

3. The food product of claim 2, wherein the food product provides calcium in the range of 100-650 mg.

4. The food product of claim 3, wherein the calcium is about 500 mg.

5. The food product of claim 3, wherein the calcium is 100-490 mg.

6. The food product of claim 1 wherein the range of Vitamin $D_3$ is 200-1200 IU.

7. The food product of claim 1, wherein the food product is enrobed with a flavored coating.

8. The food product of claim 1, wherein less than 100% of the calcium source has a particle size less than 100 µm.

9. The food product of claim 8, wherein less than 99% of the calcium source has a particle size less than 40 µm.

10. The food product of claim 9, wherein less than 90% of the calcium source has a particle size less than 20 µm.

11. The food product of claim 1, wherein the food product is selected from a group consisting of a baked food product, an unbaked food product, a cooked food product, an uncooked food product, a confectionary, a flavored cake, a brownie, and a strudel.

12. The food product of claim 11, wherein the food product has a baked or confectionary interior.

13. The food product of claim 11, wherein the food product is enrobed with a flavored coating.

14. The food product of claim 11, wherein the food product has a flavor selected from a group consisting of chocolate, chocolate mint, lemon, caramel, cappuccino, mocha, cinnamon, maple, butter, fruit flavors, vanilla, peanut butter, and carrot cake flavor.

15. The food product of claim 13, wherein the coating has a flavor selected from a group consisting of chocolate, chocolate mint, lemon, caramel, cappuccino, mocha, cinnamon, maple, butter, fruit flavors, vanilla, and peanut butter.

16. The food product of claim 1, wherein the food product has a weight in the range of 3.5 to 24 grams.

17. The food product of claim 8, wherein the food product is completely enrobed with 0.5-8 grams of coating.

18. The food product of claim 1 further comprising:
a chewable food product in which at least one piece of the food product is a delivery system for active compounds, beneficial oils and fats, dietary supplements, or additives;
wherein the food product has a water activity of less than 0.8 and the food product is a cake product; and
wherein the food product has a mouth feel, texture and taste substantially similar to a non-enriched food product.

19. The food product of claim 18, wherein the active compounds are minerals and/or vitamins.

20. The food product of claim 18, wherein the beneficial oils and fats are selected from a group consisting of partially hydrogenated palm kernel oil, palm oil, soybean oil, lecithin, monoglycerides of fatty acids, diglycerides of fatty acids, triglycerides of fatty acids, and monoesters of fatty acids.

21. The food product of claim 18, wherein the active compounds are further selected from a group consisting of antioxidant compounds, glucosamine, and chondroitin.

22. The food product of claim 18, wherein the additives are selected from a group consisting of caffeine, flavor masking agents, microencapsulated active compounds, and light, heat or temperature liable compounds.

23. The food product of claim 18, wherein the food product is enrobed with a flavored coating.

24. The food product of claim 18, wherein the food product is selected from a group consisting of a baked food product, an unbaked food product, a cooked food product, an uncooked food product, a confectionary, a flavored cake, a brownie, and a strudel.

25. The food product of claim 24, wherein the food product has a bakery or confectionary interior.

26. The food product of claim 24, wherein the food product is enrobed with a flavored coating.

27. The food product of claim 24, wherein the food product has a flavor selected from a group consisting of chocolate, chocolate mint, lemon, caramel, cappuccino, mocha, cinnamon, maple, butter, fruit flavors, vanilla, peanut butter, and carrot cake flavor.

28. The food product of claim 26, wherein the coating has a flavor selected from a group consisting of chocolate, chocolate mint, lemon, caramel, cappuccino, mocha, cinnamon, maple, butter, fruit flavors, vanilla, and peanut butter.

29. The food product of claim 18, wherein each piece of unenrobed food product has a weight in the range of 3.5 to 24 grams.

30. The food product of claim 26, wherein each piece of the food product is completely enrobed with 0.5-8 grams of coating.

31. The food product of claim 19, wherein the minerals are selected from a group consisting of magnesium, manganese, zinc, iron, and phosphorus.

32. The food product of claim 19, wherein the vitamins are selected from a group consisting of Vitamin A, the Vitamin B group, Vitamin C, D and K.

33. The food product of claim 1 wherein the food product further comprises pharmaceuticals;
wherein the food product has a shelf life of 1-26 months.

34. The food product of claim 33, wherein the pharmaceuticals are selected from a group consisting of phenyltoin, colchicine, ibuprofen, aspirin, hydroxychloroquine, and diuretics.

35. The enriched food product of claim 20, wherein the beneficial oils and fats further comprise or is replaced by DHA (docosahexaenoic acid), omega 6 fatty acid and omega 3 fatty acid.

* * * * *